(12) United States Patent
Brink (10) Patent No.: US 6,417,649 B1
(45) Date of Patent: Jul. 9, 2002

(54) SYSTEM AND METHOD FOR CHARGING A CAPACITOR USING A CONSTANT FREQUENCY CURRENT WAVEFORM

(75) Inventor: Gregory D. Brink, Port Townsend, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 67 days.

(21) Appl. No.: 09/620,446

(22) Filed: Jul. 20, 2000

(51) Int. Cl.⁷ ................................................. H02J 7/00
(52) U.S. Cl. ...................................................... 320/166
(58) Field of Search ................................. 320/106, 166

(56) References Cited

U.S. PATENT DOCUMENTS 5,625,291 A * 4/1997 Brink et al. ................. 320/131
5,725,560 A * 3/1998 Brink ............................ 607/5
6,181,102 B1 * 1/2001 Andrews et al. ............ 320/106

* cited by examiner

Primary Examiner—Edward H. Tso
Assistant Examiner—Pia Tibbits (57) ABSTRACT

A system and method for charging a high-voltage capacitor through the application of current having magnitude that has a fixed frequency waveform. During a charging sequence in which the current is applied to the capacitor, the duty cycle of the fixed frequency current waveform is dynamically controlled based on the voltage state of the capacitor to modify the energy transfer according to the efficiency with which energy can be delivered to the capacitor. This optimizes the capacitor charging sequence, increasing the speed with which the high voltage capacitor is charged. Generally, energy is transferred from a power source to the capacitor via a magnetic element such as a fly-back transformer. A pulsed voltage supply provides voltage pulses having a constant frequency and an adjustable duty cycle to a primary winding of the transformer. Initially, there is no energy stored in the transformer core. As a result, the duty cycle of the initial voltage pulse is of sufficient duration to accumulate stored energy in the transformer core. Once a predetermined quantity of energy is stored in the transformer, the transformer is controlled to generate a current to charge the capacitor. The magnitude of the current has a fixed frequency and variable duty cycle waveform.

32 Claims, 9 Drawing Sheets

SYSTEM AND METHOD FOR CHARGING A CAPACITOR USING A CONSTANT FREQUENCY CURRENT WAVEFORM

RELATED APPLICATIONS

The following application is related to the present application and its disclosure is incorporated herein by reference:

U.S. Utility Patent Application Ser. No. 09/619,954 entitled "System and Method for Charging A Capacitor Using a Variable Frequency, Variable Duty Cycle Current Waveform," filed concurrently herewith, and naming as inventor Gregory D. Brink.

BACKGROUND OF THE INVENTION

1. Field of the Invention

The present invention relates generally to charging capacitors and, more particularly, to a method and apparatus for charging high voltage capacitors.

2. Related Art

Sudden cardiac arrest has been attributed to over 350,000 deaths each year in the United States, making it one of the country's leading medical emergencies. Worldwide, sudden cardiac arrest has been attributed to a much larger number of deaths each year. One of the most common and life threatening consequences of a heart attack is the development of a cardiac arrhythmia, commonly referred to as ventricular fibrillation. When in ventricular fibrillation, the heart muscle is unable to pump a sufficient volume of blood to the body and brain. The lack of blood and oxygen to the brain may result in brain damage, paralysis or death to the victim.

The probability of surviving a heart attack or other serious heart arrhythmia depends on the speed with which effective medical treatment is provided. If prompt cardiopulmonary resuscitation is followed by defibrillation within approximately four minutes of the onset of symptoms, the probability of survival can approach or exceed fifty percent. Prompt administration of defibrillation within the first critical minutes is, therefore, considered one of the most important components of emergency medical treatment for preventing death from sudden cardiac arrest.

Cardiac defibrillation is an electric shock that is used to arrest the chaotic cardiac contractions that occur during ventricular fibrillation, and to restore a normal cardiac rhythm. To administer such an electrical shock to the heart, defibrillator pads are placed on the victim's chest, and an electrical impulse of the proper magnitude and shape is administered to the victim through the pads. While defibrillators have been known for years, they have typically been complicated, making them suitable for use by trained personnel only.

More recently, portable and transportable automatic and semi-automatic external defibrillators (generally, AEDs) for use by first responders have been developed. A portable defibrillator allows proper medical care to be given to a victim earlier than preceding defibrillators, increasing the likelihood of survival. Such portable defibrillators may be brought to or stored in an accessible location at a business, home, aircraft or the like, available for use by first responders. With recent advances in technology, even a minimally trained individual can operate conventional portable defibrillators to aid a victim in the critical first few minutes subsequent to the onset of sudden cardiac arrest.

As noted, effective medical treatment must be administered promptly after the onset of symptoms. One time consuming defibrillator operation is the charging of a high voltage capacitor that provides the energy for producing the electric shock. Unfortunately, conventional AEDs do not efficiently charge the high voltage capacitor, consuming valuable time preparing to provide the therapy. This limits the number of multiple shocks that can be administered to a patient in the minimal time available. What is needed, therefore, is a defibrillator that can charge a high voltage capacitor quickly and efficiently.

SUMMARY OF THE INVENTION

The present invention is a system and method for charging a high-voltage capacitor through the application of a current, the magnitude of which has a fixed frequency waveform. During a charging sequence in which the current is applied repeatedly to the capacitor, the duty cycle of the fixed frequency current waveform is controlled dynamically based on the capacitor voltage. Specifically, the rate at which the energy is transferred to the capacitor is modified according to the efficiency at which the energy can be delivered to the capacitor. This increases the speed at which the high voltage capacitor is charged. Alternative or additional significant benefits may be realized depending on the desired application. For example, systems implementing the present invention can provide charge times comparable to conventional systems using smaller components, a lower energy power source, a higher impedance power source or any reasonable combination thereof Generally, energy is transferred from a power source to the high voltage capacitor via a magnetic element such as an inductor or transformer. For example, a pulsed voltage supply provides voltage pulses having a constant frequency and an adjustable duty cycle to a primary winding of a fly-back transformer. Initially, there is no energy stored in the transformer core. As a result, the duty cycle of the initial voltage pulse is of sufficient duration to accumulate stored energy in the transformer core. As the quantity of energy stored in the transformer core increases, the transformer is controlled to generate a current to charge the capacitor. The magnitude of the current has a fixed frequency and variable duty cycle waveform.

Specifically, immediately subsequent to the initial accumulation of energy in the transformer core, the duty cycle of the current magnitude waveform is substantial. Since the secondary winding is out of phase with the primary winding (a fly-back transformer), the voltage waveform to cause the generation of such a current magnitude waveform has a substantially small duty cycle. Driving the transformer in such a manner maintains stored energy in the transformer core while providing the secondary winding with sufficient time to transfer energy to the capacitor as the secondary winding cannot otherwise do so in a time-efficient manner due to the minimal capacitor voltage. As the capacitor voltage increases, the duty cycle of the current waveform is decreased in response to an increase in the duty cycle of the voltage waveform. This optimizes the energy transfer rate because the speed at which such transfers can occur increases with an increase in capacitor voltage. Thus, as energy is transferred from the transformer core to the capacitor, a concomitant transfer of energy from the power source to the transformer core occurs. This operating mode is referred to herein as a "continuous mode" since this operational mode insures the transformer core continually stores energy.

A number of aspects of the invention are summarized below, along with different embodiments that may be implemented for each of the summarized aspects. It should be understood that the summarized embodiments are not necessarily inclusive or exclusive of each other and may be combined in any manner in connection with the same or different aspects that are non-conflicting and otherwise possible. These disclosed aspects of the invention, which are directed primarily to high performance capacitor charging systems and methodologies, are exemplary aspects only and are also to be considered non-limiting.

In one aspect of the invention a system for charging a high-voltage capacitor through the application of current the magnitude of which has a fixed frequency waveform is disclosed.

In another aspect of the invention, a high-voltage capacitor charging system is disclosed. The system generates current pulses having a fixed frequency magnitude. In this aspect of the invention, during a charging sequence in which the current pulses are repeatedly applied to a capacitor, the duty cycle of the fixed frequency current waveform is controlled dynamically based on the voltage of the high voltage capacitor.

In a further aspect of the invention, a system for charging a high-voltage capacitor is disclosed. In this aspect of the invention, the system includes a flyback transformer and a pulsed voltage supply. The transformer includes a core, a primary winding and a secondary winding. The pulsed voltage supply provides to the primary winding a voltage having a constant frequency, adjustable duty cycle waveform. The initial duty cycle of the voltage waveform is of sufficient duration to accumulate a quantity of stored energy in the transformer core, after which the voltage waveform is continually applied to the primary coil. The duty cycle of the voltage waveform increases from a substantially small value to a substantially large value during the charging sequence in response to an increase in the instantaneous voltage of the high voltage capacitor.

In a still further aspect of the invention, a system for charging a high-voltage capacitor is disclosed. In this aspect of the invention, the system includes a transformer and a pulsed voltage supply. The transformer includes a core, a primary winding and a secondary winding. A capacitor is electrically coupled across the secondary winding. The pulsed voltage supply provides to the primary winding a voltage having a constant frequency, adjustable duty cycle waveform.

The duty cycle of the voltage waveform is modified dynamically such that energy is stored continually in the transformer core as the capacitor is charged. In particular, during individual cycles of a charging sequence, the system transfers energy from the pulsed voltage supply to the transformer core to replace energy transferred previously from the transformer core to the high voltage capacitor.

In a still further aspect of the invention, a capacitor charging system is disclosed. In this aspect of the invention, the system includes a capacitor charger connected to a capacitor and a diode electrically connected to and interposed between the capacitor and the capacitor charger. The diode has a cathode connected to the capacitor and an anode connected to the capacitor charger. The capacitor charger charges the capacitor by generating a current the magnitude of which has a fixed frequency, variable duty cycle waveform.

In one embodiment of this aspect of the invention, the capacitor charging system includes a magnetic element across which the capacitor is connected, and a pulsed voltage supply connected to a node of the magnetic element, with the other node of the magnetic element connected to ground. The pulsed voltage supply provides to the primary winding a charging voltage that transitions between a first voltage and second voltage that is less than the first voltage at a substantially constant frequency and with a variable duty cycle.

The magnetic element may be a fly-back transformer. In such implementations, the transformer includes a core, a primary winding and a secondary winding that is out of phase with the primary winding. Here, the capacitor is connected across the secondary winding. In one particular implementation, the capacitor charger includes a current sensor connected in series between the other primary winding node and ground. The current sensor generates a voltage having a magnitude that is indicative of current flowing through the primary winding. The charger also includes a control circuit that is operationally coupled to the pulsed voltage supply and the current sensor. The control circuit provides a duty cycle adjust signal to the pulsed voltage supply to adjust the duty cycle of the charging voltage waveform based on the current magnitude signal.

In a further aspect of the invention, a capacitor charger for charging a high voltage capacitor is disclosed. The charger includes a capacitor charging transformer and a charging circuit. The transformer includes a core with primary and secondary windings. The high voltage capacitor is electrically connected across the secondary winding through a diode. The charging circuit is connected to the primary winding and applies a voltage across the primary winding to cause a current to flow through the secondary winding such that the transformer continually stores energy in its core. The secondary winding current transfers energy from the transformer core to the high voltage capacitor.

In another aspect of the invention, a method for charging a capacitor is disclosed. The method includes providing to the capacitor a current the magnitude of which has a fixed frequency waveform. In one embodiment, the duty cycle of the fixed frequency current waveform is varied. The method may also include the steps of: driving a primary winding of a transformer with a fixed frequency, variable duty cycle voltage waveform; sensing an electric current flowing through the primary winding; and adjusting the duty cycle of the voltage waveform when the electric current flowing in the primary winding reaches a predetermined value.

Various embodiments of the present invention provide certain advantages and overcome certain drawbacks of the conventional techniques. Not all embodiments of the invention share the same advantages and those that do may not share them under all circumstances. This being said, the present invention provides numerous advantages including the noted advantage of rapidly transferring energy to a high-energy capacitor. Adjusting the duty cycle of fixed frequency current pulses applied to a capacitor enables energy to be transferred quickly to the capacitor as compared with conventional techniques. In addition, the present invention eliminates the need to sense when the secondary winding of the capacitor-charging transformer has transferred substantially all of its energy to the capacitor. The present invention also eliminates the need to have complex feedback circuitry for adjusting the current in the primary winding of the transformer based on a sensor input from the secondary winding of the transformer. These and other features and advantages of the present invention as well as the structure and operation of various embodiments of the present invention are described in detail below with reference to the accompanying drawings.

BRIEF DESCRIPTION OF THE DRAWINGS

This invention is pointed out with particularity in the appended claims. The above and further features and advantages of this invention may be better understood by referring to the following description when taken in conjunction with the accompanying drawings. In the drawings, like reference numerals indicate identical or functionally similar elements. Additionally, the left most one or two digits of a reference numeral identify the drawing in which the reference numeral first appears.

In the drawings.

DETAILED DESCRIPTION

Figure 1A:
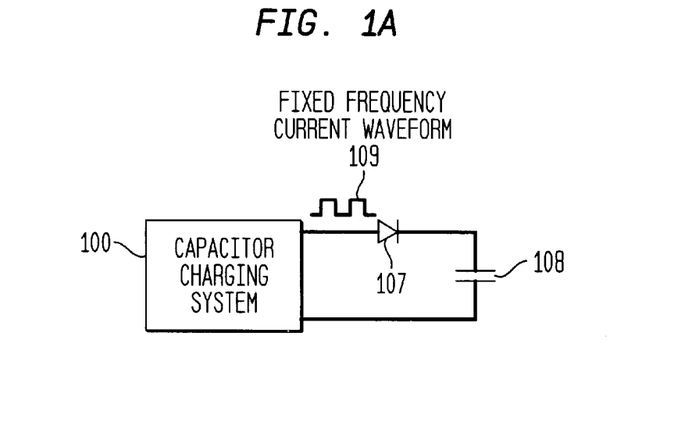
FIG. 1A is a high level block diagram of a capacitor charging system in accordance with one embodiment of the present invention.

The present invention is directed to a system and method for charging a high-voltage capacitor. FIG. 1A is a high-level block diagram of a capacitor charging system in accordance with one embodiment of the present invention. Capacitor charging system 100 generates a current 109 the magnitude of which has a fixed frequency waveform. During a charging sequence in which current 109 is applied to high voltage capacitor 108, the duty cycle of the fixed frequency current waveform is controlled dynamically to modify the energy transfer characteristics according to the rate at which energy can be delivered to capacitor 108.

Figure 1B:
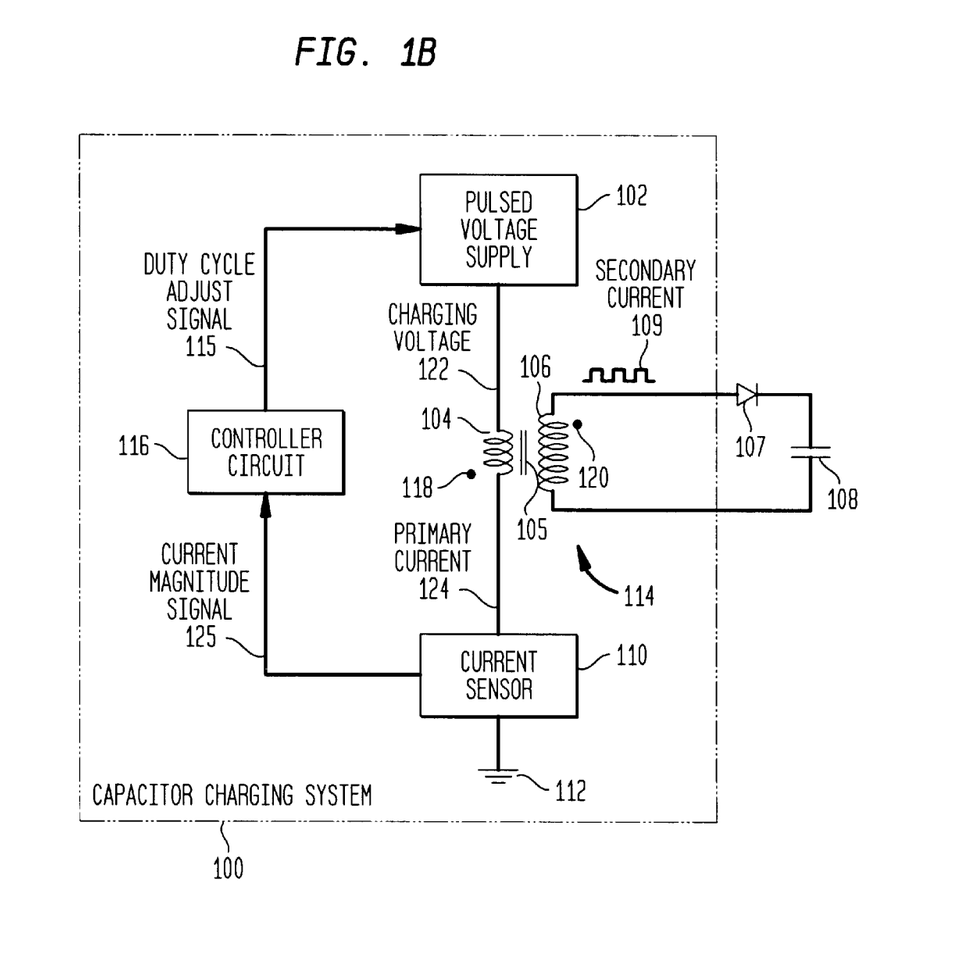
FIG. 1B is a block diagram of one embodiment of the capacitor charging circuit of the present invention.

As will be described in greater detail below, the present invention may utilize a magnetic element to transfer energy to a high voltage capacitor. FIG. 1B is a block diagram of one embodiment of a capacitor charging system 100 of the present invention utilizing a magnetic element. In this illustrative embodiment, capacitor-charging system 100 includes a transformer 114 as such a magnetic element. It should become apparent from the present disclosure, however, that other magnetic elements as well as other current generators may be utilized in accordance with the teachings of the present invention.

Capacitor charging transformer 114 includes a core 105, primary winding 104 and secondary winding 106. In the particular embodiment illustrated in FIG. 1B, primary winding 104 and secondary winding 106 form a fly-back transformer and, therefore, are out of phase as shown by the polarity indicating indicia 118 and 120.

As such, the following description sets forth various embodiments and components of system 100 for driving fly-back transformer 114 to generate the fixed frequency, variable duty cycle current waveform 109. Such a current flows through secondary winding 106 to transfer energy to capacitor 108 connected across secondary winding 106 through fly-back diode 107.

As primary current 124 flows through primary winding 104 and the energy stored in transformer core 105 increases, current 109 does not flow from secondary winding 106 to capacitor 108. Conversely, when current does not flow through primary winding 104, current 109 flows from secondary winding 106 to capacitor 108 to charge capacitor 108. Thus, primary winding 104 transfers energy from a power source to transformer core 105 when current flows through primary winding 104 and, conversely, secondary winding 106 passes energy from transformer core 105 to capacitor 108 when current 109 flows through secondary winding 106.

Charging system 100 includes a pulsed voltage supply 102 connected in series with primary winding 104 of capacitor charging transformer 114. In embodiments utilizing a fly-back transformer, current waveform 109 is generated by controlling the voltage across primary winding 104. Thus, in this embodiment, pulsed voltage supply 102 generates a charging voltage waveform 122 having a substantially constant frequency and an adjustable duty cycle. Initially, however, there is no energy stored in the transformer core. As a result, the duty cycle of the initial voltage pulse is of sufficient duration to accumulate stored energy in transformer core 105. Once a predetermined quantity of energy is stored in transformer core 105, transformer 114 is controlled in accordance with the teachings of the present invention to generate current 109 to charge capacitor 108. In accordance with the present invention, the magnitude of current 109 has a fixed frequency and, preferably, a variable duty cycle waveform.

Specifically, immediately subsequent to an initial accumulation of energy in transformer core 105, the duty cycle of the current waveform 109 is substantial. Since secondary winding 106 is out of phase with primary winding 104, then, charging voltage waveform 122 has a substantially small duty cycle. In one embodiment, for example, the duty cycle is approximately 0.5 to 4 percent. This maintains stored energy in transformer core 105 while providing secondary winding 106 with sufficient time to transfer energy to capacitor 108 as secondary winding 106 cannot do so in a time-efficient manner due to the minimal capacitor voltage. As the capacitor voltage increases, the duty cycle of the current waveform 109 is decreased to optimize the energy transfer as the rate at which such transfers can occur increases with an increase in capacitor voltage. In the illustrative embodiment, this occurs in response to a corresponding increase in the duty cycle of charging voltage 122. Thus, as energy is transferred from the transformer core 105 to the capacitor 108, a concomitant transfer of energy from the power source to the transformer core occurs. This operating mode is referred to herein as a "continuous mode" since transformer core 105 continually stores energy during the charging sequence.

Charging system 100 further includes a current sensor 110 connected in series between primary winding 104 and ground 112. Current sensor 110 produces a current magnitude signal 125 indicative of current 124 flowing in primary winding 104 to a control circuit 116. As described in further detail below, control circuit 116 adjusts the duty cycle of charging voltage 122 through the provision of duty cycle adjust signal 115 to pulsed voltage supply 102. Responsive to signal 115, pulsed voltage supply 102 adjusts the duty cycle of charging voltage waveform 122. As will be described in detail below, in the illustrative embodiment, the duty cycle is controlled by pulsed voltage supply 102 as a function of whether primary current 124 is above or below a predetermined level additional or alternative control conditions may also be considered in alternative embodiments.

Figure 2:
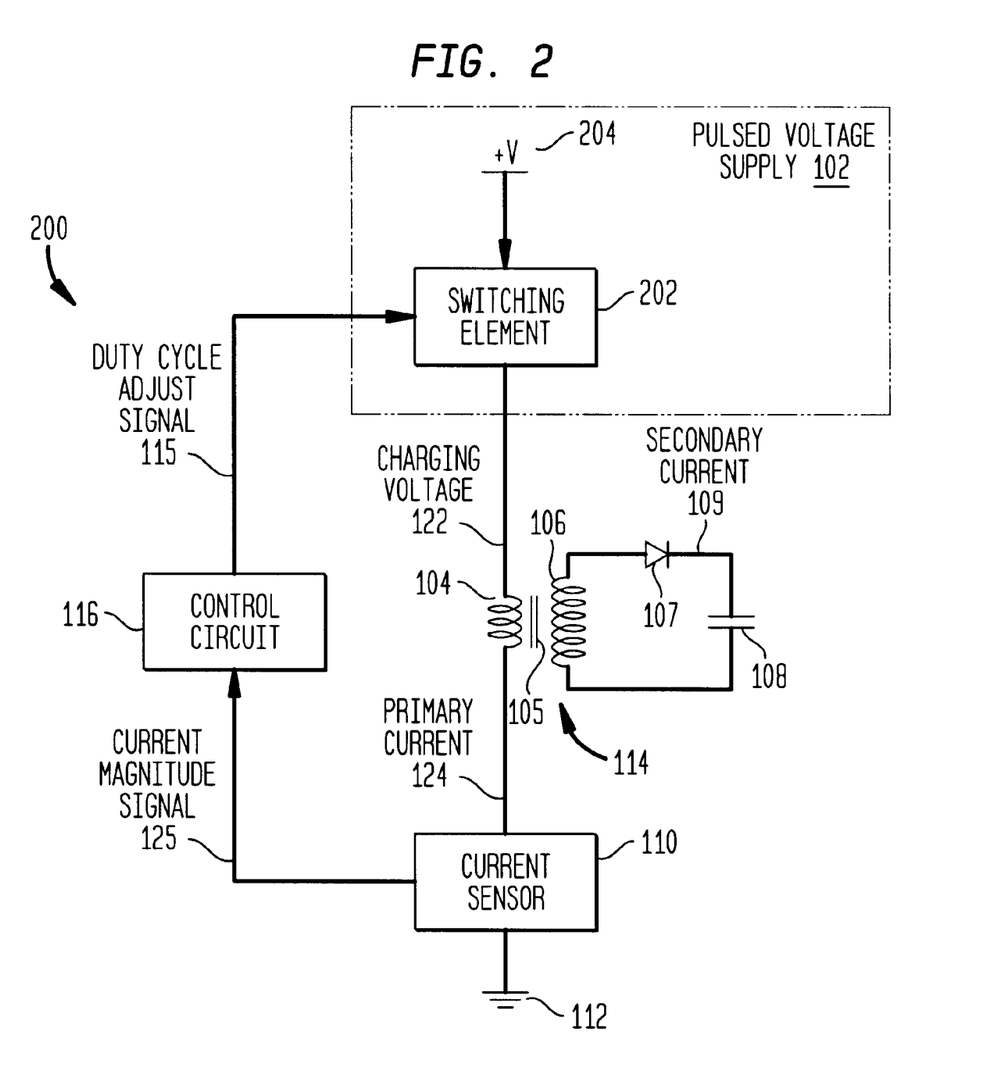
FIG. 2 is a block diagram of another embodiment of the present invention.

FIG. 2 is a block diagram of another embodiment of a capacitor charging system 200 of the present invention. In this embodiment, pulsed voltage supply 102 includes a constant voltage source 204 and a switching element 202 connected in series between voltage source 204 and primary winding 104. Constant voltage source 204 may be any source of power such as a battery, a direct current power supply, etc. In one preferred embodiment, voltage source 204 is a lithium battery.

Switching element 202 interrupts the electrical connection between voltage source 204 and primary winding 104 in response to duty cycle adjust signal 115 to effect a desired change in the duty cycle of voltage signal 122 and, hence, secondary current 109. Switching element 202 preferably includes a switch that provides a small series resistance to the anticipated primary current 124 such that there is a minimal voltage drop across switching element 202. This allows substantially all voltage generated by voltage source 204 to be applied to primary winding 104.

In addition, switching element 202 preferably provides a switching waveform that has sufficiently smooth rising and falling edges to prevent overshoot and ringing from occurring on switched charging voltage waveform 122. Furthermore, switching element 202 is preferably characterized by a turn-off time (in response to signal 115) sufficiently fast to substantially avoid over-charging and saturating core 105 of capacitor charging transformer 114. As would be obvious to one of ordinary skill in the art, many other implementations of switching element 202 now or later developed may be utilized in accordance with the present invention.

Figure 3:
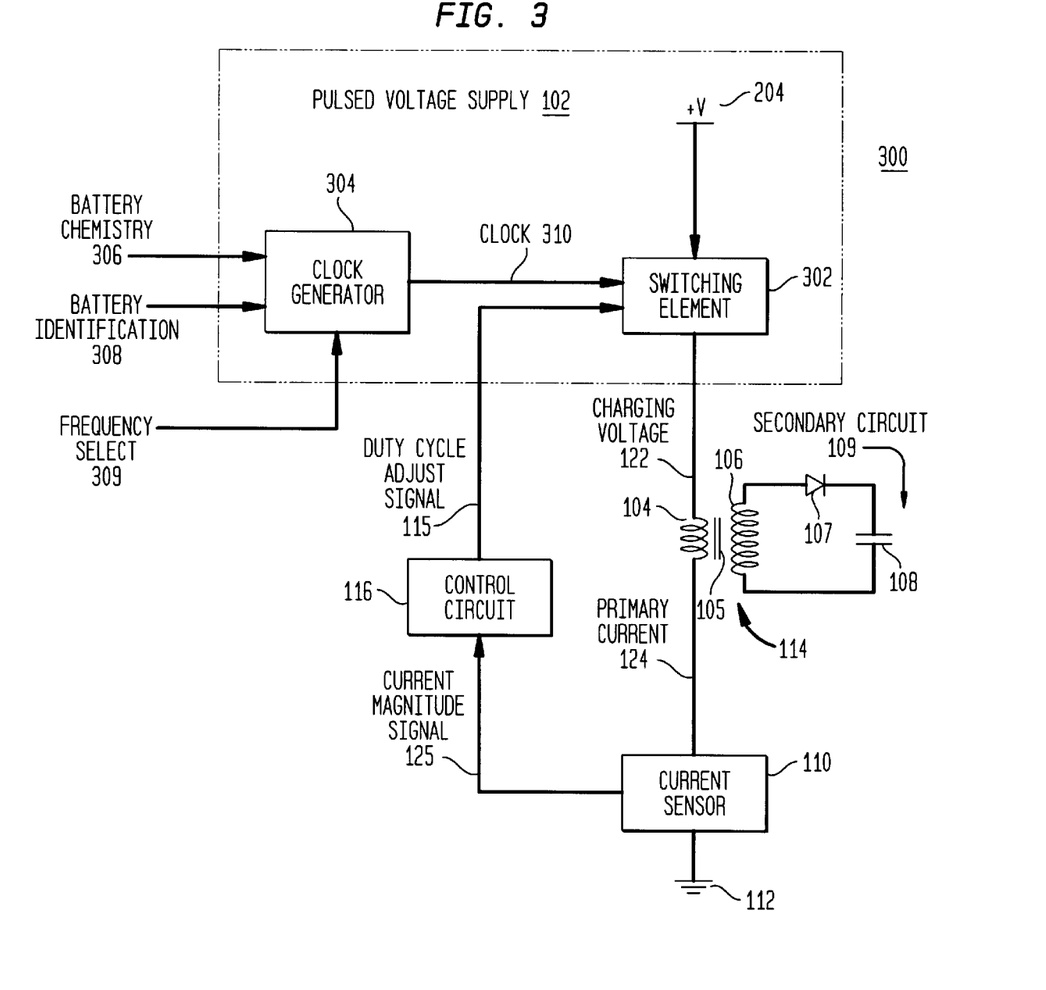
FIG. 3 is a block diagram of another embodiment of the present invention.

FIG. 3 is a block diagram illustrating another embodiment of the capacitor charging system 100 (FIG. 1) of the present invention, referred to generally as capacitor charging system 300. System 300 includes a particular embodiment of pulsed voltage supply 102. Here, pulsed voltage supply 102 includes a clock generator 304 and a switching element 302 having an input from clock generator 304 and an input from control circuit 116. Clock generator 304 provides a clock signal 310 having a substantially constant frequency to switching element 302. Preferably, the frequency of clock signal 310 may be selected from a plurality of different frequencies as shown by frequency select line 309. The frequency of clock signal 310 may then be adjusted to optimize the transfer of energy as described herein.

The amount of current drawn from constant voltage supply 204 is proportional to the frequency of charging voltage 122 applied to primary winding 104. In one implementation of the present invention, voltage source 204 is a battery pack. Batteries have particular chemistries and are manufactured by certain manufacturers. Certain batteries require discharge currents to be lower than other batteries. For example, some manufacturers include an internal thermal fuse in the battery pack. Discharging a current too quickly from such batteries can result in a rapid increase in the battery pack temperature. This will cause the thermal fuse to open and the battery pack to become disabled. Additionally, certain battery chemistries allow deeper and more rapid discharges than others. For example, nickel cadmium batteries allow more rapid and deep discharges as compared to lithium batteries. Therefore, if lithium batteries are used to charge capacitor 108, a lower clock frequency is used in order to prevent the lithium battery from failing during use. Therefore, in a preferred embodiment of the present invention, clock generator 304 produces frequencies designed in concert with the current limitations of the installed battery pack.

In one preferred embodiment, the frequency of clock signal 310 is determined by clock generator 304 based on the type of battery pack currently utilized. In this embodiment, clock generator 304 preferably receives as an input a battery chemistry signal 306 and a battery identification signal 308. Battery chemistry signal 306 indicates the chemistry of the installed battery pack while battery identification 308 identifies the manufacturer of the installed battery pack. Based on this information, clock generator 304 adjusts the frequency of clock signal 310.

Figure 4:
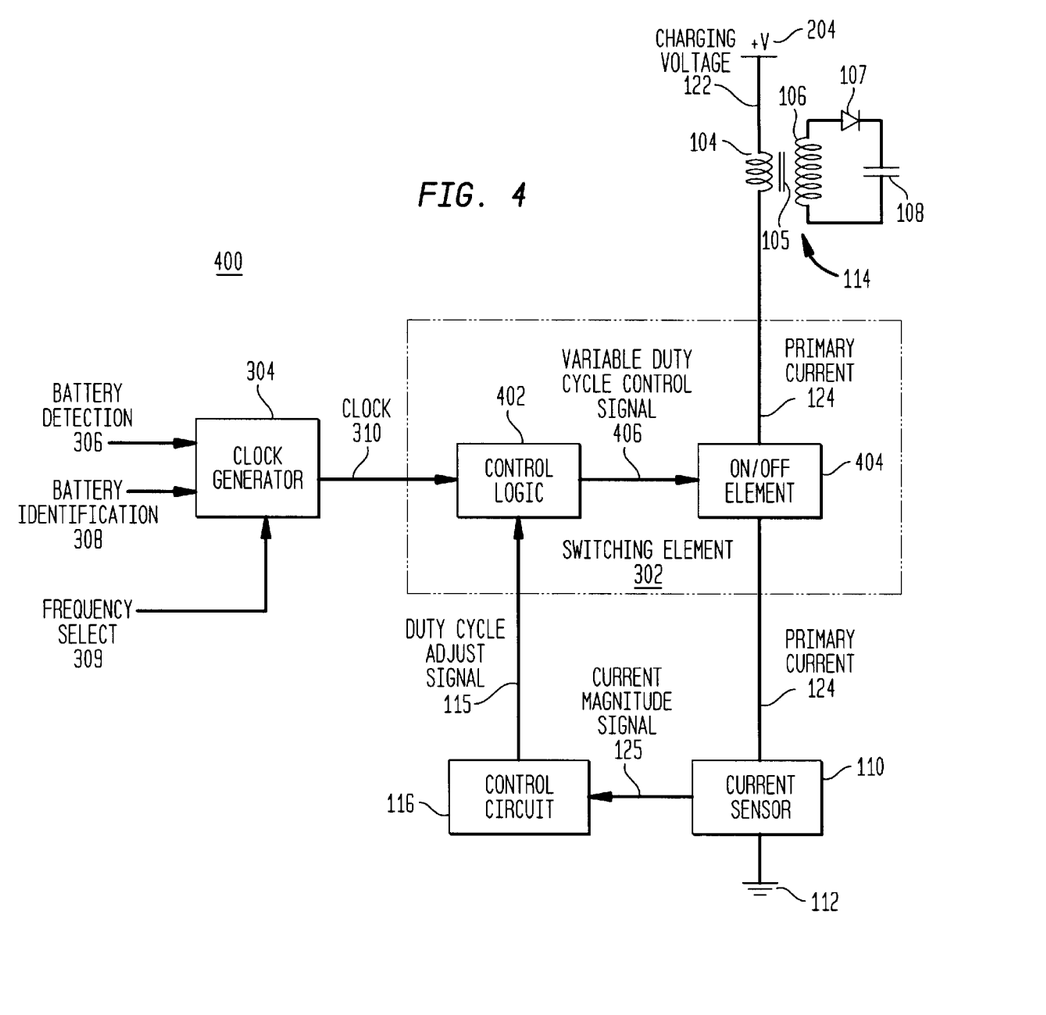
FIG. 4 is a block diagram of another embodiment of the present invention.

FIG. 4 is a block diagram of an alternative embodiment of a capacitor charging circuit of the present invention referred to generally as capacitor charging circuit 400. Capacitor charging circuit 400 includes a switching element 302 that includes control logic circuit 402 and an on/off circuit element 404. In this embodiment, switching element 302 is electrically interposed between primary winding 104 and current sensor 110, rather than between primary winding 104 and voltage source 204. Control logic 402 receives clock signal 310 generated by clock generator 304, and a duty cycle adjust signal 115 generated by control circuit 116. Control logic 402 provides a variable duty cycle control signal 406 to on/off element 404 based on these inputs. Control logic 402 provides an "on" signal to on/off element 404 allowing current 124 to flow through primary winding 104 until there is either a change in state of clock signal 310 or a change in the state of duty cycle adjust signal 115. In the illustrative embodiment, the "on" signal is a positive voltage or a logic 1. The "off" signal then is the inverse of the "on" signal; that is, it is a near-zero voltage or a logic 0.

As noted, control circuit 116 may consider any number of factors to control duty cycle adjust signal 115 in accordance with embodiments of the present invention.

In this embodiment, control circuit 116 changes the state of duty cycle adjust signal 115 when current magnitude signal 125 indicates that primary current 124 has reached a predetermined value. This change of state by control circuit 116 causes control logic 402 to turn on/off element 404 "off" earlier in the "on" clock cycle of clock signal 310. When signal 125 from current sensor 110 indicates a current level lower than the maximum current level, control circuit 116 changes the state of signal 115, returning to its initial state. This causes control logic 402 to turn "on" on/off element 404 in response to the next "on" period of clock 310. It would be obvious to one of ordinary skill in the art to modify this aspect of the present invention to provide a negative logic system, where in a "on" state is a logic 0 and an "off" state is a logic 1.

Figure 5:
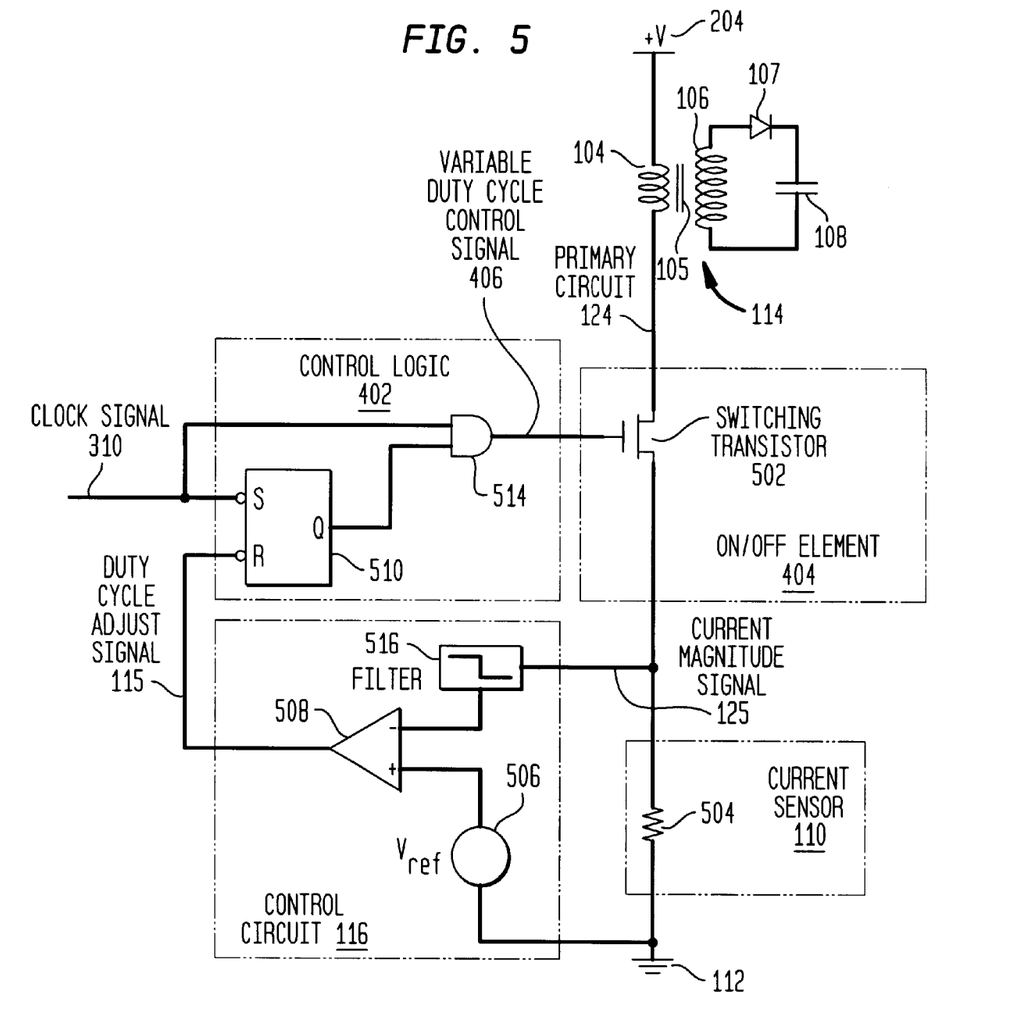
FIG. 5 is electronic schematic diagram of one aspect of the present invention.

FIG. 5 is a simplified schematic circuit diagram of an embodiment of the invention illustrated in FIG. 4. In this embodiment, on/off element 404 includes a switching transistor 502 and current sensor 110 includes a sense resistor 504. In this implementation, clock signal 310 is gated with a set-reset flip-flop 510 to insure that variable duty cycle control signal 406 has a single pulse during each charge cycle, and has a duty cycle that is determined by the duty cycle of clock signal 310.

Control circuit 116 includes a voltage comparator 508 having one input coupled to a voltage reference 506. The voltage from sense resistor 504 is coupled to another input of voltage comparator 508, preferably through a filter 516. Control logic 402 includes a set-reset flip-flop 510 and AND gate 514. Switching transistor 502 is connected in series between primary winding 104 and sense resistor 504, with sense resistor 504 being connected to electrical ground 112. The output of voltage comparator 508 is connected to a reset input of flip-flop 510. Clock signal 310 is connected to a set input of flip-flop 510 and also is connected to an input of AND gate 514. The Q output of flip-flop 510 is coupled to a second input of AND gate 514. The output of AND gate 514, variable duty cycle control signal 406, drives a control input of switching transistor 502.

AND gate 514 controls the signal 406 being passed to switching transistor 502. When the Q output from S-R flip-flop 510 is logic 1, gate 514 passes clock signal 310 to the gate of switching transistor 502. Thus, switching transistor 502 will be operated so as to produce voltage pulses in phase with clock signal 310. If the Q output from flip-flop 510 is a logic 0, then gate 514 outputs a logic 0 and turns off switching transistor 502, preventing current 124 from flowing. Logic 0 occurs when comparator output of voltage comparator 508 changes state, causing the Q output of flip-flop 510 to be reset to logic 0. This occurs when current 124 passing through primary winding 104 has increased to the point where the voltage across sense resistor 504 exceeds voltage reference 506.

Referring now to control circuit 116, filter 516 couples the voltage produced across sense resistor 504 to the first input of voltage comparator 508. When primary winding 104 of capacitor charging transformer 114 is switched on, the leakage inductance in the winding will produce a current spike at the instant the voltage increases. Filter 516 is designed to filter out this spike without substantially affecting the remainder of the signal. In one embodiment of the present invention, filter 516 is a single pole R-C low-pass filter having a corner frequency at least equal to the frequency of clock signal 310. It would be obvious to those of skill in the art that other filters may be used as well. For example, active analog low-pass filters, switched capacitor filters, or digital filters could be used. In one embodiment, a digital blanking filter is used. The digital blanking filter would sample the waveform at the sense resistor, and would provide a low output to the comparator until the digital filter determined that the current spike had passed. The digital filter would then pass the voltage signal without any attenuation or phase distortion. In another embodiment, the digital blanking filter would ignore the magnitude of the waveform for a predetermined period of time. After the predetermined time has passed, the blanking filter would then pass the voltage signal without attenuation.

Voltage comparator 508 in one embodiment of present invention may be selected on the basis of the speed at which it changes state and the amount of overshoot that occurs during the switching process. It is important for the comparator 508 to have a faster response time than the speed at which current 124 increases. If comparator 508 is slower than the rising current, the current will continue to rise after reaching the selected maximum value. On the next cycle of the voltage applied to the primary winding, primary current 124 will increase from an initial value that may exceed voltage reference 506. This will cause comparator 508 to change state; however, the energy stored in primary winding 104 has increased due to the continued application of primary current flowing through primary winding 104. Thus, the stored energy will continue to increase through each subsequent cycle until the transformer saturates, MOSFET switching transistor 502 suffers a breakdown due to the high current, or other components overly stressed by the larger than expected current breakdown. In one preferred embodiment of present invention voltage comparator 408 is a Max998 comparator manufactured by Maxim, Inc. Another component, MOSFET switching transistor 502, preferably has a sufficient current capacity to switch the selected maximum primary current 124 through primary winding 104 and should be able to withstand transient currents caused by the inductance when the voltage applied to primary winding 104 transitions. In one embodiment of the present invention, MOSFET switching transistor 502 is an IRF2807 transistor manufactured by International Rectifier, Inc.

Figure 6:
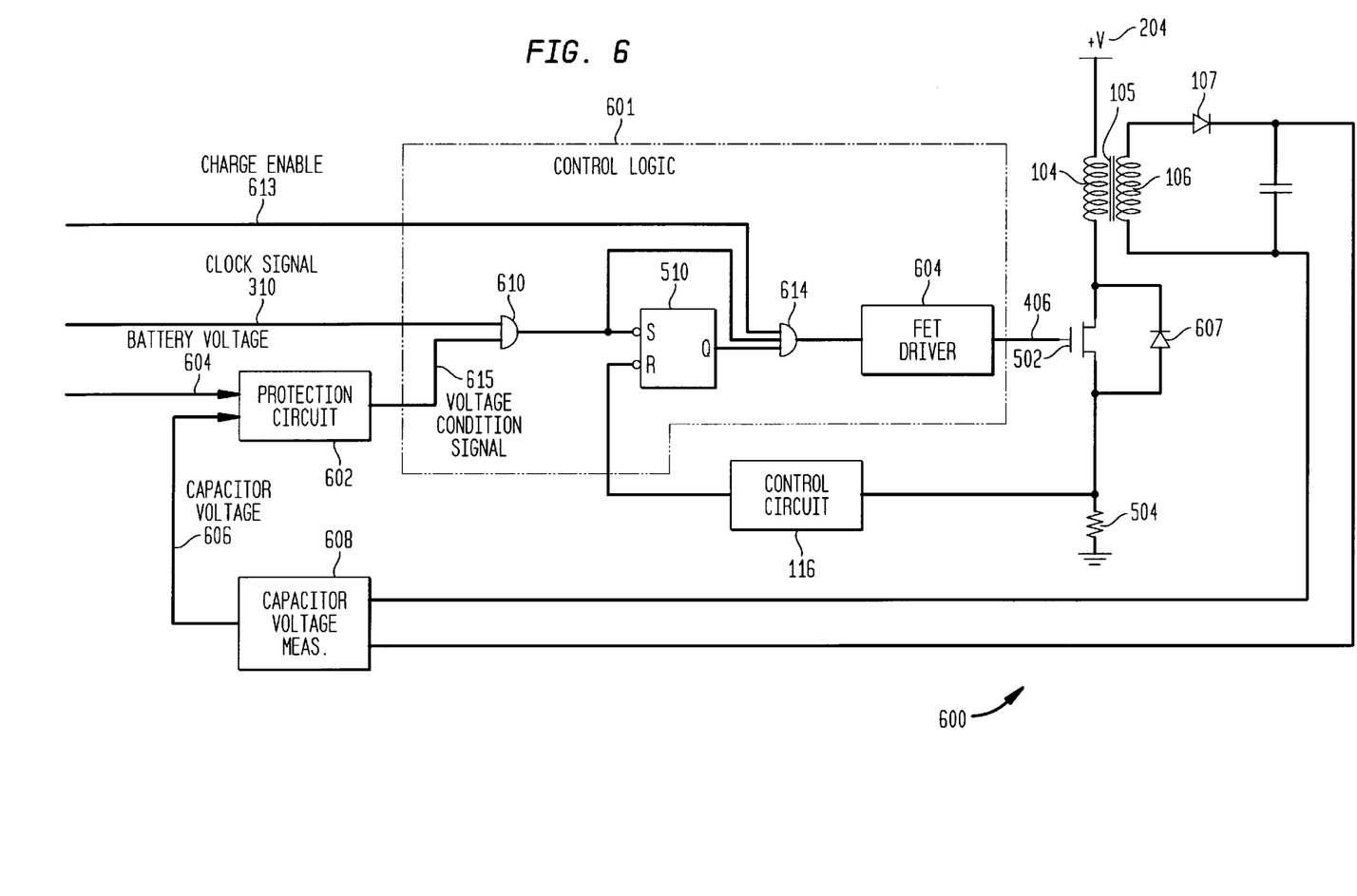
FIG. 6 is a schematic block diagram of one aspect of the present invention.

FIG. 6 is an alternative embodiment of the capacitor charging system of the present invention, referred to generally as capacitor charging system 600. In charging system 600, a clock signal 310 is coupled to a first input of an AND gate 610 of control logic 601. A battery under-voltage and a capacitor over-voltage protection circuit 602 provides a second input to AND gate 610. Battery voltage signal 604 may be determined using any well known technique. Capacitor voltage signal 606 is generated by a capacitor voltage measurement circuit 608 that receives inputs connected across capacitor 108. Capacitor voltage measurement circuit 608 may be implemented in any well-known manner.

If the battery and capacitor voltages 604, 606 are within the proper limits, voltage condition signal 615 is generated by protection circuit 602. Voltage condition signal 615 is provided to AND gate 610. This will cause AND gate 610 to output a logical 0. This signal will be propagated through AND gate 614 and will turn off MOSFET driver 604. MOSFET driver 604 will in turn cease supplying current to MOSFET switching transistor 502, turning it off to open the primary winding circuit.

If the battery and capacitor voltages are within the necessary limits, clock signal 310 will be passed to AND gate 614 and the S input of S-R flip-flop 510. In this embodiment, a third input is provided to AND gate 614 from charge enable signal 613. A logic zero on the charge enable signal 613 will provide a logic 0 to AND gate 614, and will turn off MOSFET driver 604. If both the Q output and charge enable signal 613 provide a logic 1 to AND gate 614, clock signal 310 will be passed to the input of MOSFET driver 604. Thus MOSFET driver 604 will turn on MOSFET switching transistor 502 in phase with clock signal 310. As described above, when flip-flop 510 is reset, that is, the Q output changes to a logic 0, AND gate 614 will output a logic 0 to the input of MOSFET driver 604. This will turn off MOSFET switching transistor 502 and interrupt the voltage pulse supplied to MOSFET switching transistor 502.

MOSFET switching transistor 502 has a transient suppressor diode 607 connected across its drain and source in order to provide a current path for discharging primary winding 104 leakage inductance when the transistor is turned off. This is to prevent a leakage inductance of the primary winding 104 from generating a voltage sufficiently high to destroy MOSFET switching transistor 502.

It should be understood that protection circuit 602 and capacitor voltage measurement circuit 608 described above may be implemented in any well known manner now or later developed. Such implementations are apparent to those of ordinary skill in the art and, therefore, are not described further herein.

Figure 7:
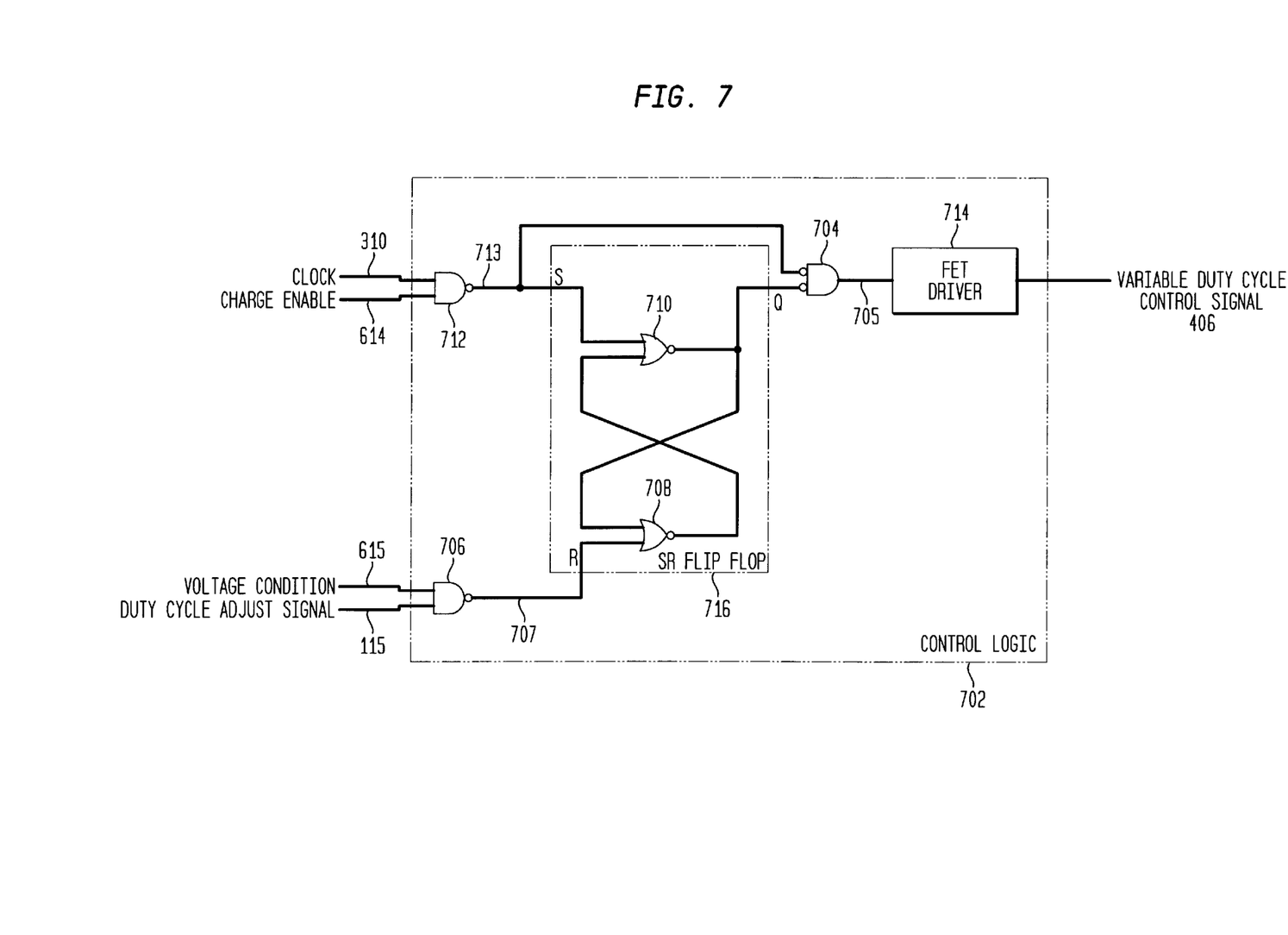
FIG. 7 is a schematic diagram of one embodiment of the capacitor charging circuit control logic illustrated in FIG. 5.

FIG. 7 is a schematic diagram of another embodiment of control logic 601, referred to herein as control logic 702. As with the embodiment illustrated in FIG. 6, clock signal 310 is gated with set-reset flip-flop 510 to insure signal 406 is a single pulse during each charge cycle, and has a maximum duty cycle determined by the duty cycle of clock signal 310.

In this embodiment, an S-R flip-flop 716 is implemented with NOR gates 710, 708. The set (S) and reset (R) inputs receiving signals from NAND gates 712 and 706, respectively. The Q output of S-R flip-flop 716 and NAND gate 712 are provided to a NOR gate 704 to drive a FET driver 714 which, in turn, generates variable duty cycle control signal 406. In this embodiment, FET driver 714 is controlled by positive logic. That is, when signal 705 is a logic "high", driver 714 will turn on; when signal 705 is a logic "low", driver 714 will turn off.

During a charging cycle, as primary current 124 increases toward the threshold value, the state of flip-flop 716 remains unchanged. When primary current 124 exceeds the threshold value, duty cycle adjust signal 115 will change from a high to a low state. This will be inverted by NAND gate 706 to apply a "high" state value to NOR gate 708. This will force flip-flop 716 to change state, thereby causing a "high" state signal to be applied to NOR gate 704. This, in turn, will force NOR gate 704 into a "low" state output, terminating the drive signal to FET driver 714. This will cause FET switch 502 to turn off, preventing current from flowing through the primary winding 104 of transformer 114. This, as noted, allows secondary winding 106 of transformer 114 to begin to charge capacitor 108. When clock signal 310 is deasserted, latch 716 is set. Latch 716 is reset when the overcurrent threshold is reached, terminating the control signal pulse.

Transformer 114 is selected according to several design trade-offs. One desirable characteristic of transformer 114 is that it have a high turns ratio. Such a transformer produces a high output voltage for a much lower applied or input voltage. In addition, in the disclosed aspects of the capacitor charging system 100, the windings of transformer 114 are of opposite polarity. This results in little or no current flowing in secondary winding 106 of the transformer while primary winding 104 is accumulating energy. When primary winding 104 has completed its charge cycle and is turned off, secondary winding 106 will then transfer energy into capacitor 108, as described above. In selecting the size of transformer 114 and the optimal frequency for charging clock signal 310 several factors should be considered. For example, the energy storage within core 105 of transformer 114 is a function both of the inductance of primary winding 104 and the voltage that is applied to it. In general, the larger the core 105 of transformer 114, the more energy that may be stored within the magnetic field surrounding it. In addition, there is a current at which magnetic core 105 of transformer 114 will saturate; applying a current above this value will not improve circuit performance. In general the larger the transformer core, the higher the saturation current. Therefore, selection of transformer 114 will often times involve balancing physical and electrical requirements of the system. A larger transformer will allow lower frequencies to be used because the larger transformer will be able to utilize larger currents and will therefore transfer energy at a greater rate per cycle than a smaller transformer. This reduces the demand on the supporting components; they may operate, for example, at a lower speed. However, a larger transformer will occupy a large volume of space, weigh more, and may produce more heat and may produce electrically interfering noise if large currents are passed through it. On the other hand, a smaller transformer will require higher frequencies in order to transfer an equivalent amount of energy. This is because a smaller transformer utilizes lower currents and hence transfers energy at a lower rate per cycle. However, using a higher frequency to achieve an equivalent rate of energy transfer requires greater complexity due to parasitic characteristics, noise sensitivity, etc. In one embodiment of the present invention, transformer 114 has an Lp of approximately 8 $\mu$H and a turns ratio of 1:38 (primary:secondary).

Figure 8A:
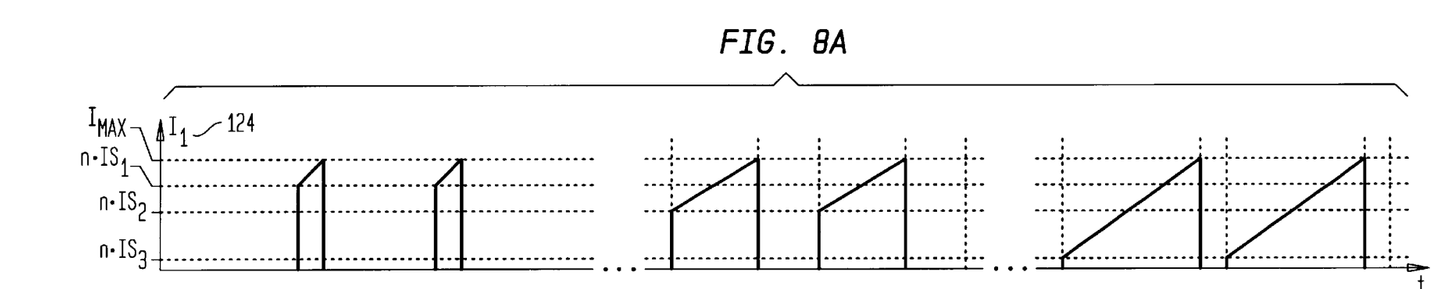
FIGS. 8A–8C are exemplary waveforms in one embodiment of the present invention.
Figure 8B:
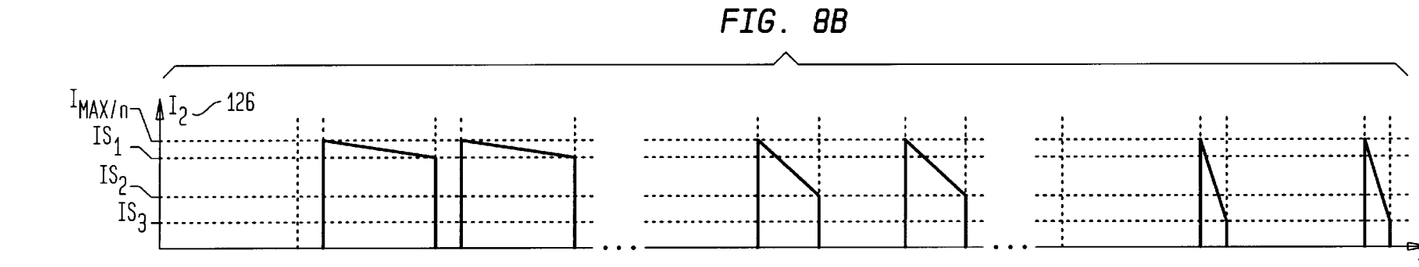
Figure 8C:
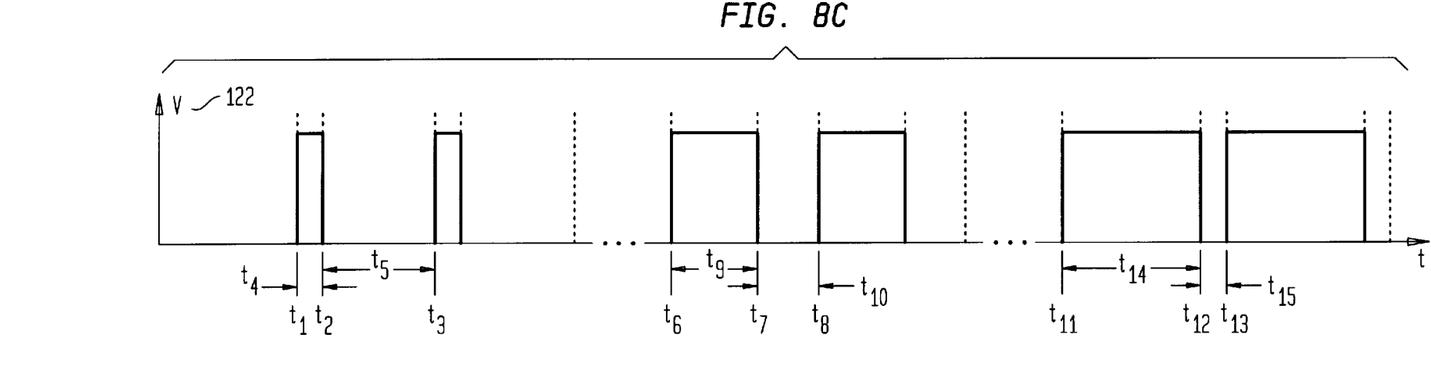

FIGS. 8A–8C illustrate exemplary waveforms generated in accordance with one embodiment of the present invention. The exemplary waveforms include primary current 124 flowing in primary winding 104 (FIG. 8A), secondary current 126 flowing in secondary winding 106 (FIG. 8B) and charging voltage 122 applied to primary winding 104 (FIG. 8C). Two cycles of each waveform are illustrated, each set of cycles occurring at different times during a charging sequence, as indicated by the series of dots interposed between separate time intervals.

As noted, initially, transformer core 105 has minimal or no energy stored therein. To store a desired quantity of energy in transformer core 105, primary current 124 is ramped from zero to a predetermined maximum value $I_{max}$ immediately upon the invocation of a charging sequence. The waveforms illustrated in FIGS. 8A–8C occur subsequent to the initial storage of energy in transformer core 105. The waveforms illustrate the changing duty cycle of the fixed frequency variable duty cycle current waveform 109 of the present invention. It should be noted that in these Figures, current waveform 109 is the same as secondary current 109 since capacitor 108 is connected across secondary winding 106.

As will be described below, the duty cycle of primary current waveform 124 is controlled such that secondary current 109 is applied to capacitor 108 for greater durations when the voltage across the capacitor and, hence, the rate of energy transfer to the capacitor is low, and for lesser durations as the capacitor voltage increases. The energy transferred to the capacitor 108 is stored in transformer core 105. As shown in FIG. 8A, the rate at which the energy is transferred into transformer core 105 is substantially constant throughout the charging sequence, as shown by the constant slope of the primary current waveforms. On the other hand, the rate of energy transfer from transformer core 105 to capacitor 108 increases as the capacitor voltage increases. This is shown by the increasing negative slope of the secondary current waveform illustrated in FIG. 8B.

The duty cycle of the primary and secondary current waveforms is adjusted to achieve energy transfer equilibrium, thereby maintaining the transformer in a continuous conduction mode of operation throughout the charging sequence. The current that flows through each winding during a charging cycle is a function of the turns ratio, n, of transformer 114. Generally, primary current 124 starts at a value that is generally equivalent to the product of the turns ratio and secondary current 126 at the end of the immediately previous cycle. Primary current 124 ramps from this value to $I_{max}$ during the first portion of the charge cycle. Similarly, for each charging cycle, secondary current 126 is equivalent to the immediately occurring primary current 124 divided by the turns ratio. Secondary current 126 ramps down from this value to some lower value over the remaining portion of the charge cycle.

Referring to the Figures, charging voltage 122 is applied to primary winding 104 for time duration $t_4$ beginning at time $t_1$ and ceasing at time $t_2$. At time $t_2$, primary current 124 has reached the predetermined maximum value $I_{max}$. In response, pulsed voltage supply 102 is turned off at time $t_2$ as shown by the falling edge of charging voltage waveform 122. At this time, primary winding current 124 falls to zero and secondary current 126 in secondary winding 106 rises to a level of $I_{max}/n$, where n is the turns ratio of transformer 114. Secondary current 126 begins to decrease as the energy stored in transformer core 105 is transferred to capacitor 108. This occurs for time duration $t_5$. As noted, in this embodiment, secondary winding 106 is out of phase with primary winding 104 and, therefore, transfers energy when primary winding 104 is not being charged; that is, time period $t_4$ and time period $t_5$ occur during one charging cycle defined by one period of charging voltage 122.

As noted, the energy transfer rate is proportional to the rate at which secondary current 126 decreases; that is, the magnitude of the slope of secondary current waveform 126 during time period $t_5$. During this time period, secondary current 126 decreases from $I_{max}/n$ to $I_{s1}$. Time period $t_5$ is determined by the choice of frequency of constant frequency clock signal 310. At time $t_3$, constant frequency clock signal 310 (not shown) changes state, applying main charging voltage 122 to primary winding 104, as shown in FIG. 8C. This, in turn, causes current to flow through primary winding 104, and discontinues the discharging of secondary winding 106. This is shown by primary current waveform 124 linearly increasing, not from a zero current value, but from initial condition $n*I_{s1}$, where n is the turns ratio of transformer 114.

FIGS. 8A–8C each show the respective waveforms at some later time at which the capacitor voltage is greater than during time intervals $t_4$ and $t_5$. At this later time $t_6$, constant frequency clock signal 310 changes state, applying main charging voltage 122(FIG. 8C) to primary winding 104 for time duration $t_9$ beginning at time $t_6$ and ceasing at time $t_7$. At time $t_7$, primary current 124 has reached the predetermined maximum value $I_{max}$. In response, pulsed voltage supply 102 is turned off at time $t_7$ as shown by the falling edge of charging voltage waveform 122. At this time, primary winding current 124 falls to zero and secondary current 126 in secondary winding 106 rises to a level of $I_{max}/n$. Secondary current 126 begins to decrease as the energy stored in transformer core 105 is transferred to capacitor 108. This occurs for time duration $t_{10}$ during which secondary current 126 decreases from $I_{max}/n$ to $I_{s2}$. Comparison with secondary waveform occurring at time interval $t_5$ illustrates a change in slope of secondary current 126. This change in slope reflects the increased energy transfer rate now possible given the increased capacitor voltage. As a result, secondary current 126 decreases from $I_{max}$ to $I_{s2}$ that is less than $I_{s1}$ during a time interval $t_{10}$ that is less than time interval $t_5$.

At time $t_8$, constant frequency clock signal 310 changes state, applying main charging voltage 122 to primary winding 104, as shown in FIG. 8C. This, in turn, causes current to flow through primary winding 104, and discontinues the discharging of secondary winding 106. This is shown by primary current waveform 124 linearly increasing from initial condition $n*I_{s2}$ where n is the turns ratio of transformer 114.

FIGS. 8A–8C each shown the respective waveforms at some still later time at which the capacitor voltage is greater than during time intervals $t_4$, $t_5$ and $t_9$, $t_{10}$. At this later time $t_{11}$, main charging voltage 122 is applied to primary winding 104 for time duration $t_{14}$ beginning at time $t_{11}$ and ceasing at time $t_{12}$. At time $t_{12}$, primary current 124 has reached the predetermined maximum value $I_{max}$. In response, pulsed voltage supply 102 is turned off at time $t_{12}$ and primary winding current 124 falls to zero. Secondary current 126 rises to a level of $I_{max}/n$ at time $t_{12}$. Secondary current 126 decreases from $I_{max}/n$ to $I_{s3}$ during time duration $t_5$ as the energy stored in transformer core 105 is transferred to capacitor 108. Comparison with secondary waveform 126 occurring at time intervals $t_5$ and $t_{10}$ illustrates a continuing change in slope of secondary current 126 reflecting the continued increase in the energy transfer rate due to a further increase capacitor voltage. As a result, secondary current 126 decreases from $I_{max}$ to $I_{s3}$ that is less than $I_{s2}$ during a time interval $t_{15}$ that is less than time interval $t_{10}$. At time $t_{13}$, main charging voltage 122 increases causing current to flow through primary winding 104, and causes current to discontinue flowing through secondary winding 106. This is shown by primary current waveform 124 linearly increasing from initial condition $n*I_{s3}$.

The time to charge primary winding 104 to $I_{max}$, that is, time durations $t_4$, $t_9$, and $t_{14}$ are successively longer time periods. Conversely, the time to discharge secondary winding 106 from $I_{max}/n$ to $I_{s2}$, time durations $t_5$, $t_{10}$, and $t_{15}$ are successively shorter time durations. This insures transformer core 105 retains essentially the same amount of stored energy during the charging sequence as the energy transfer rate from transformer core 105 to capacitor 108 increases, while rapidly transferring energy from transformer core 105 to capacitor 108. This is characteristic of a transformer operating in accordance with the present invention; that is, in the continuous mode of operation wherein only the energy removed from transformer 114 is replaced, and transformer 114 is maintained so as to continually store energy.

Figure 9:
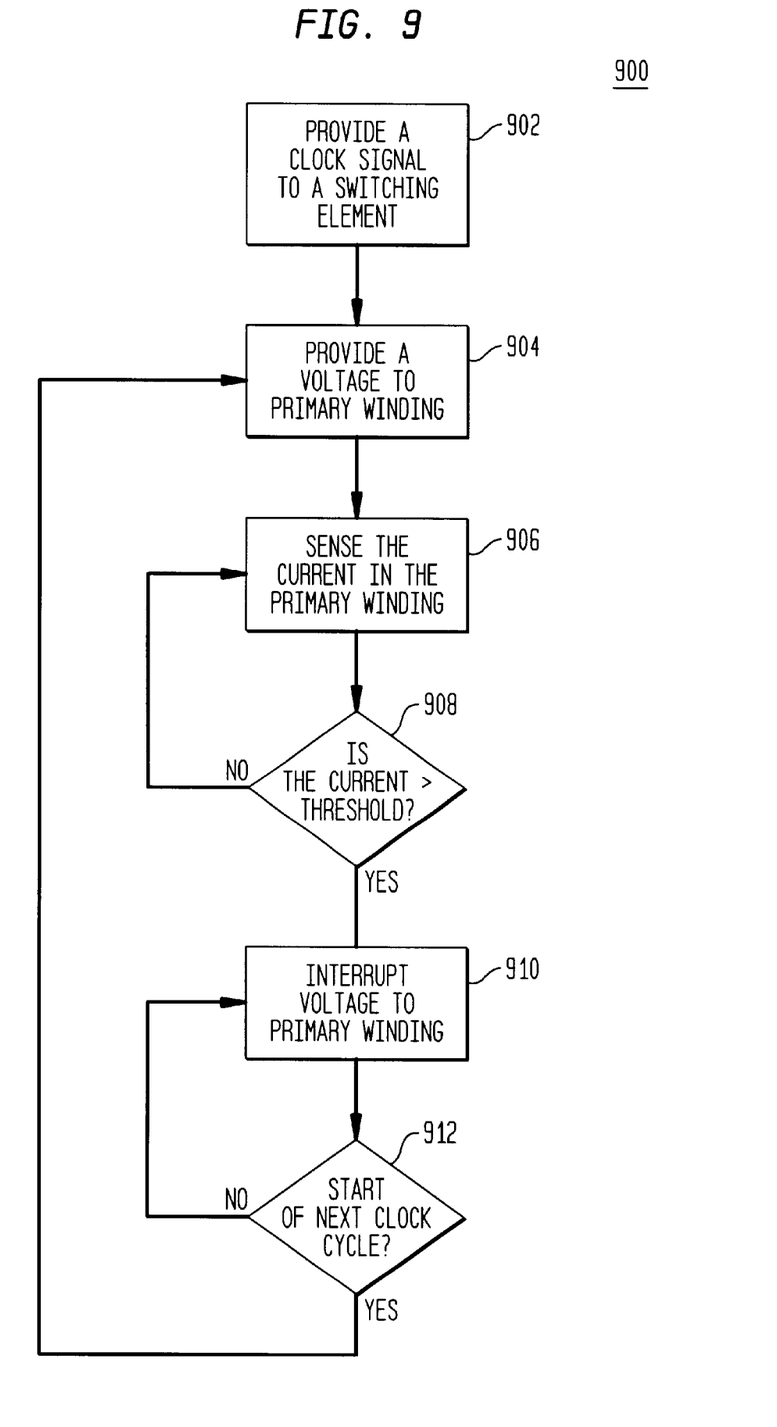
FIG. 9 is a flowchart for a process of executing one embodiment of the present invention.

FIG. 9 is a flow chart for executing a process representing one embodiment of the present invention. In steps 902 and 904, clock signal is applied to a switching element to produce a pulsed voltage waveform. This pulsed voltage waveform is then applied to the primary winding of the capacitor charging transformer, and the current in the primary winding is sensed, step 906, until it equals a predetermined threshold value, step 908. When the threshold value is reached, the voltage is interrupted, step 910, and the start of the next frequency cycle is determined, step 912, and voltage is provided again to the primary winding of the transformer, step 904.

It should be understood that, as noted, capacitor charging system 100 may take on any other configurations and implementations. For example, other circuit configurations and components may be used in addition to or instead of the above-noted configurations and components. For example, other magnetic elements such as a single inductor may be used. In other embodiments, a current regulator is used. It should also be understood that the duty cycle on time may oscillate between long and short on times under certain operating conditions. These operating conditions may arise due to the selected values of, for example, the clock frequency, transformer inductance, peak current, capacitor voltage, etc. The disclosed embodiments of the capacitor charger of the present invention provide for a significant transfer of energy to capacitor 108 in minimal time. For example, in one embodiment, the capacitor charger enables the capacitor to store up to 240 joules in less than three seconds.

The present invention is related to U.S. Utility Patent Application entitled "System and Method for Charging A Capacitor Using a Variable Frequency, Variable Duty Cycle Current Waveform," filed concurrently herewith under Attorney Docket No. 10990390-1, as naming as inventor Gregory D. Brink, the specification of which is hereby incorporated by reference in its entirety.

It should be understood that various changes and modifications of the embodiments shown in the drawings and described in the specification may be made within the spirit and scope of the present invention. Accordingly, it is intended that all matter contained in the above description and shown in the accompanying drawings be interpreted in an illustrative and not in a limiting sense. The invention is limited only as defined in the following claims and the equivalents thereto.

What is claimed is:

1. A system for charging a high-voltage capacitor through application of a current, the magnitude of the current having a fixed frequency waveform, with a duty cycle that decreases as a charging voltage of the capacitor increases during charging.

2. A high-voltage capacitor charging system constructed and arranged to generate current pulses having a fixed frequency to a capacitor, wherein during a charging sequence in which said current pulses are repeatedly applied to the capacitor, the duty cycle of the fixed frequency current waveform is controlled dynamically based on the voltage of the high voltage capacitor.

3. A system for charging a high-voltage capacitor comprising;
   a flyback transformer having a core, a primary winding and a secondary winding; and
   a pulsed voltage supply for providing to said primary winding a voltage having a constant frequency, adjustable duty cycle waveform,
   wherein an initial duty cycle of said voltage waveform is sufficiently long to accumulate a quantity of stored energy in said transformer core, after which a value of said duty cycle of said voltage waveform decreases during a charging sequence as a voltage of the high voltage capacitor increases.

4. A system for charging a high-voltage capacitor comprising;
   a transformer having a core, a primary winding and a secondary winding wherein the high-voltage capacitor is coupled across the secondary winding; and
   a pulsed voltage supply for providing to the primary winding a voltage having a constant frequency, adjustable duty cycle waveform,
   wherein said duty cycle of said voltage waveform is modified dynamically such that energy is stored continually in said transformer core as the capacitor is charged.

5. The system of claim 4, wherein, during individual cycles of a charging sequence, the system transfers energy from said pulsed voltage supply to said transformer core to replace energy transferred previously from said transformer core to the high voltage capacitor.

6. A capacitor charging system comprising:
   a capacitor charger connected to a capacitor, said capacitor charger constructed and arranged to charge the capacitor by generating a current having a magnitude that has a fixed frequency, variable duty cycle waveform; and
   a diode electrically connected to and interposed between the capacitor and said capacitor charger, said diode having a cathode connected to the capacitor and an anode connected to said capacitor charger.

7. The capacitor charging system of claim 6, wherein said capacitor charger comprises:
   a transformer having a core, a primary winding, and a secondary winding, the capacitor is coupled across the secondary winding; and
   a pulsed voltage supply connected to a node of said transformer, said pulsed voltage supply constructed and arranged to provide to said core a charging voltage that transitions between a first voltage and a second voltage that is smaller than the first voltage, wherein said charging voltage having a substantially constant frequency, and a variable duty cycle.

8. The capacitor charging system of claim 7, wherein said transformer comprises a fly-back transformer.

9. The capacitor charging system of claim 8, wherein said capacitor charger further comprises:
   a current sensor, connected to a second node of said primary winding, constructed and arranged to generate a current magnitude signal indicative of current flowing through said primary winding; and
   a control circuit, operationally coupled to said pulsed voltage supply and said current sensor, constructed and arranged to provide a duty cycle adjust signal to said pulsed voltage supply to adjust said duty cycle of said charging voltage waveform based on said current magnitude signal.

10. The capacitor charging system of claim 9, wherein said current sensor comprises:
    a current-to-voltage converter.

11. The capacitor charging system of claim 10, wherein said current-to-voltage converter includes a resistor.

12. The capacitor charging system of claim 11, wherein said current-to-voltage converter further includes an analog-to-digital converter.

13. The capacitor charging system of claim 8, wherein said pulsed voltage supply comprises:
    a voltage source for providing a voltage; and
    a switching element connected in series with said voltage source and said primary winding,
    wherein said switching element controls said voltage applied to said primary winding.

14. The capacitor charging system of claim 13, wherein said pulsed voltage supply further comprises:
    a clock generator providing a plurality of clock signal pulses, wherein a frequency of the clock signal pulses is equal to said substantially constant frequency of the pulsed voltage provided to said switching element, wherein said switching element, responsive to said clock signal pulses, provides said voltage pulses to said primary winding.

15. The capacitor charging system of claim 14, wherein said frequency of said clock signal pulses generated by said clock generator is a function of battery chemistry.

16. The capacitor charging system of claim 15, wherein said switching element comprises:
    a switching transistor.

17. The capacitor charging system of claim 16, wherein said switching transistor is a MOSFET transistor.

18. The capacitor charging system of claim 14, wherein said frequency of said clock signal pulses generated by said clock generator is a function of a particular battery manufacturer.

19. The capacitor charging system of claim 14, wherein said control circuit comprises:
    a bistable device connected to said current sensor, said bistable device constructed and arranged to change states of said duty cycle adjust signal when said current sensor indicates said current in said primary winding approximately equals a predetermined amount.

20. The capacitor charging system of claim 19,
    wherein said current sensor comprises a current-to-voltage converter, and
    wherein said reference value is a reference voltage.

21. The capacitor charging system of claim 20, wherein said current-to-voltage converter is a resistor.

22. The capacitor charging system of claim 19, wherein said control circuit further comprises:

a filter having an input from said current sensor at which said filter receives said current magnitude signal, and an output coupled to said first input of said comparator, wherein said filter attenuates at least one frequency of said current magnitude signal.

23. The capacitor charging system of claim 22, wherein said control circuit further comprises:

control logic having a first input coupled to said output of said bistable device at which said control logic receives said duty cycle adjust signal and a second input coupled to said clock generator at which said control logic receives said clock signal, and an output coupled to said switching element for controlling said duty cycle of said voltage pulses.

24. A capacitor charger for charging a high voltage capacitor comprising:

a capacitor charging transformer including a core, a primary winding and a secondary winding, the capacitor being electrically connected across said secondary winding; and a charging circuit connected to said primary winding, said charging circuit applying a voltage across said primary winding to cause a current to flow through said secondary winding such that said transformer continually stores energy in its core, wherein said current flowing through said secondary winding transfers energy from said transformer core to said high voltage capacitor.

25. The capacitor charger of claim 24, wherein said circuit comprises:

a clock generator constructed and arranged to generate a clock signal having a substantially constant frequency;

a voltage supply, responsive to said clock signal, constructed and arranged to supply to said primary winding a voltage having a fixed frequency, variable duty cycle waveform;

a current sensing element providing a current magnitude signal indicative of current flowing through said primary winding; and a controller having at least one output control signal coupled to said voltage supply for adjusting said duty cycle of said variable waveform based on said current magnitude signal.

26. The capacitor charging circuit of claim 25, wherein said voltage supply comprises:

a voltage source; and a switching transistor coupled to said voltage source and having a control input at which said clock signal is received, said transistor providing said variable duty cycle voltage waveform at said substantially constant frequency and a voltage level substantially equal to said voltage source.

27. The capacitor charging circuit of claim 25, wherein said controller comprises:

a bistable device having an input coupled to said current sensing element and an output coupled to said voltage supply, said bistable device changing state when said current sensing element indicates said current in the primary winding is substantially equal to a predetermined value, wherein said voltage supply, responsive to said change in state, adjusts said duty cycle of said voltage waveform.

28. The capacitor charging circuit of claim 25, wherein said adjustment of said duty cycle includes setting said voltage pulse to substantially zero volts.

29. A method for charging a capacitor comprising:

providing to the capacitor a current the magnitude of which has a fixed frequency waveform.

30. The method of claim 29, further comprising:

varying the duty cycle of said fixed frequency current.

31. The method of claim 30, further comprising the steps of:

driving a primary winding of a transformer with a fixed frequency variable duty cycle voltage waveform;

sensing an electric current flowing through said primary winding;

adjusting said duty cycle of said voltage waveform when said electric current flowing in said primary winding reaches a predetermined value.

32. A capacitor charger for charging a high voltage capacitor, wherein said capacitor charger is constructed and arranged to enable said capacitor to store up to 240 joules in less than three seconds.

\* \* \* \* \*